(12) United States Patent
Katsurada et al.

(10) Patent No.: US 10,933,220 B2
(45) Date of Patent: **\*Mar. 2, 2021**

(54) BALLOON CATHETER (71) Applicant: ASAHI INTECC CO., LTD., Seto (JP)

(72) Inventors: Takeharu Katsurada, Nagoya (JP); Takeshi Mogi, Owariasahi (JP)

(73) Assignee: ASAHI INTECC CO., LTD., Seto (JP)

( * ) Notice: Subject to any disclaimer, the term of this patent is extended or adjusted under 35 U.S.C. 154(b) by 161 days.

This patent is subject to a terminal disclaimer.

(21) Appl. No.: 16/269,643

(22) Filed: Feb. 7, 2019

(65) Prior Publication Data

US 2019/0167947 A1 Jun. 6, 2019

Related U.S. Application Data

(63) Continuation of application No. 14/969,958, filed on Dec. 15, 2015, now Pat. No. 10,252,028.

(30) Foreign Application Priority Data

Mar. 27, 2015 (JP) ................................. 2015-065856

(51) Int. Cl.
*A61M 25/10* (2013.01)
*A61M 25/01* (2006.01)
(Continued)

(52) U.S. Cl.
CPC .... *A61M 25/0108* (2013.01); *A61M 25/0052* (2013.01); *A61M 25/10* (2013.01);
(Continued)

(58) Field of Classification Search
CPC .......... A61M 25/0108; A61M 25/0052; A61M 25/10; A61M 25/1006; A61M 25/1079;
(Continued)

(56) References Cited

U.S. PATENT DOCUMENTS 4,878,492 A 11/1989 Sinofsky et al.
4,981,478 A * 1/1991 Evard ................. A61M 25/005
600/585
(Continued)

FOREIGN PATENT DOCUMENTS

CN 102258824 A 11/2011
EP 1 721 631 A1 11/2006
(Continued)

OTHER PUBLICATIONS

Feb. 1, 2019 Office Action issued in Chinese Patent Application No. 201510946020.2.
(Continued)

*Primary Examiner* — Kathleen S Holwerda
(74) *Attorney, Agent, or Firm* — Oliff PLC (57) ABSTRACT

A balloon catheter includes a balloon and an inner shaft. The inner shaft includes a marker member arranged on an outer periphery of a coil body having a sparsely wound portion in which gaps are formed between adjacent windings of the wire of the coil body. A distal end part and a proximal end part of the marker member are arranged at a position facing a void formed within one of the gaps between the adjacent windings of the wire of the coil body. The inner shaft of the balloon catheter therefore will not buckle, preventing damage to the balloon by contact with the marker member when the balloon catheter is passed through the inside of a curved blood vessel.

6 Claims, 6 Drawing Sheets

(51) Int. Cl.
*A61M 25/00* (2006.01)
*A61B 90/00* (2016.01)

(52) U.S. Cl.
CPC . *A61M 25/1006* (2013.01); *A61B 2090/3966* (2016.02); *A61M 2025/1079* (2013.01)

(58) Field of Classification Search
CPC ... A61M 2025/1079; A61B 2090/3966; A61B 2017/22001
See application file for complete search history.

(56) References Cited

U.S. PATENT DOCUMENTS

| | | | |
|---|---|---|---|
| 5,951,539 | A | 9/1999 | Nita et al. |
| 6,285,903 | B1 * | 9/2001 | Rosenthal ............... A61B 6/12 600/424 |
| 10,252,028 | B2 * | 4/2019 | Katsurada ............. A61M 25/10 |
| 2004/0153049 | A1 * | 8/2004 | Hewitt ............. A61M 25/0012 604/527 |
| 2006/0129045 | A1 * | 6/2006 | Warnack ................ A61F 2/958 600/435 |
| 2006/0259011 | A1 * | 11/2006 | Kubo ............... A61M 25/0108 604/526 |
| 2012/0271232 | A1 | 10/2012 | Katsurada et al. |

FOREIGN PATENT DOCUMENTS

| | | |
|---|---|---|
| EP | 2 389 973 A1 | 11/2011 |
| EP | 2 517 749 A1 | 10/2012 |
| EP | 2 719 418 A1 | 4/2014 |
| EP | 2 762 192 A1 | 8/2014 |
| JP | H01-141676 A | 6/1989 |
| JP | 3219968 B2 | 10/2001 |
| JP | 3659664 B2 | 6/2005 |
| JP | 2006-501969 A | 1/2006 |
| JP | 2006-314623 A | 11/2006 |
| JP | 2011-244905 A | 12/2011 |
| WO | 2004/033015 A1 | 4/2004 |

OTHER PUBLICATIONS

Jul. 29, 2016 Extended European Search Report issued in European Application No. 16154293.1.
Jul. 24, 2017 Office Action Issued in U.S. Appl. No. 14/969,958.
Jan. 16, 2018 Office Action issued in U.S. Appl. No. 14/969,958.
Apr. 26, 2018 Office Action issued in Japanese Patent Application No. 2015-065856.
Aug. 3, 2018 Office Action issued in U.S. Appl. No. 14/969,958.

\* cited by examiner

BALLOON CATHETER

CROSS REFERENCE TO RELATED APPLICATIONS

This is a Continuation of application Ser. No. 14/969,958 filed Dec. 15, 2015, which claims priority to Japanese Application No. 2015-065856 filed Mar. 27, 2015. The disclosure of the prior applications is hereby incorporated by reference herein in its entirety.

BACKGROUND

The disclosed embodiments relate to a medical device. Specifically, the disclosed embodiments relate to a balloon catheter to be inserted into a stenosis site inside a blood vessel for expanding the stenosis site.

Balloon catheters to be inserted into a stenosis site inside a blood vessel for expanding the stenosis site have already been proposed. A balloon catheter mainly comprises a balloon as an expanding body, an outer shaft joined to a proximal end of the balloon, and an inner shaft inserted within the balloon and the outer shaft. Further, a metal marker member having radiopacity is commonly provided inside the balloon so that the position of the balloon can be detected under exposure of irradiation.

For example, Japanese Patent No. 3659664 discloses a catheter for expanding a blood vessel. The catheter includes a platinum contrast marker (a marker member) attached to a medical tube (an inner shaft) comprising an inner layer, a coil layer as a reinforcement layer, and an outer layer.

As another example, Japanese Patent No. 3219968 discloses a balloon-expandable catheter having an inner tube (an inner shaft) and a balloon. A radiopaque marker fits in the inside of a depressed groove arranged on an outer periphery of the inner tube in the inside of the balloon. The radiopaque marker is covered by a heat-shrinkable tube. Moreover, also disclosed is a balloon-expandable catheter in which the radiopaque marker is arranged on the outer periphery of an inner tube not having a depressed groove. Here too, the radiopaque marker is covered by a heat-shrinkable tube.

However, the catheter for expanding a blood vessel disclosed in Japanese Patent No. 3659664 has the following disadvantages. Since the marker member is attached to the outer periphery of the inner shaft and is exposed to an inner periphery of the balloon, there is a risk that an end portion of the marker member may damage the balloon. Further, a difference in rigidity may arise when a flexible inner shaft and a highly rigid marker member are used, creating a risk that the inner shaft will buckle due to an excessively concentrated stress at the attachment position of the marker member.

Moreover, in the balloon-expandable catheter disclosed in Japanese Patent No. 3219968 above, processing steps such as polishing and etching are required for providing a depressed groove. Therefore, the manufacturing process will be disadvantageously complicated. Further, disadvantageously, a site where the depressed groove is provided tends to have decreased strength due to the reduction in cross-sectional area. Furthermore, since the outer diameter of a balloon portion will be larger for a configuration in which the radiopaque marker is arranged on the outer periphery of the inner tube and is covered by a heat-shrinkable tube, the diameter of the balloon catheter cannot be easily reduced. Further, disadvantageously, in a case where the marker member is made of a highly rigid metal, the marker member itself cannot be easily deformed as required to follow the curvature of a blood vessel and the like, and the portion of the balloon catheter at which the marker member is arranged may easily become stuck in the blood vessel.

SUMMARY

Accordingly, an object of the disclosed embodiments is to provide a balloon catheter in which there is no risk of damaging the balloon, and in which a diameter of a portion where the marker member is arranged can be reduced. Additionally, it is an object of the disclosed embodiments to prevent the portion of the balloon catheter where the marker member is arranged from becoming stuck even when inserted into a curved blood vessel.

A balloon catheter of the disclosed embodiments comprises a balloon and an inner shaft joined to the balloon. The inner shaft comprises an inner layer, a coil body arranged at an outer periphery of the inner layer and having a sparsely wound portion where a wire is sparsely wound, a marker member arranged at an outer periphery of the coil body, and an outer layer covering the coil body and the marker member. At least a portion of one of a distal end part and a proximal end part of the marker member is arranged at a position facing a void formed between adjacent windings of the wire of the sparsely wound portion.

When the above balloon catheter in this configuration is inserted into a curved blood vessel, at least a portion of one of the distal end part and the proximal end part of the marker member can enter into the void formed between adjacent windings of the wire of the coil body. Therefore, a stress concentration generated at a location where the marker member is arranged can be relieved, preventing the inner shaft from buckling. Further, the end portions (the distal end part and the proximal end part) of the marker member can be prevented from projecting toward the inner periphery of the balloon. Moreover, the manufacturing process is simplified because the marker member is covered by the outer layer without requiring the use of another member. Furthermore, there is no risk that the marker member will damage the balloon. In addition, because the outer layer covering the coil body also serves to cover the marker member, an outer diameter of the inner shaft can be kept small.

Further, at least one of the distal end part and the proximal end part of the marker member is preferably curved toward the inner shaft. In this configuration, at least one of the distal end part and the proximal end part forms a smooth and continuous tapered shape. Therefore, rupture (burst or breakage) of the balloon due to contact with the marker member can be prevented. Further, even in a case where external force is applied to the marker member when the balloon catheter curves, an edge of the marker member can enter into the void and make contact with the wire of the coil body, allowing the movement of the marker member to be controlled.

In the balloon catheter of the disclosed embodiments, there is no risk of damaging the balloon of the balloon catheter, and the diameter of the portion where the marker member is arranged can be reduced. Additionally, the portion of the balloon catheter where the marker member is arranged will not get stuck in the blood vessel even when the blood vessel is curved.

DETAILED DESCRIPTION OF EMBODIMENTS

Below, balloon catheters according to the disclosed embodiments will be described in detail. However, the present invention shall not be limited to those embodiments, and modifications in design can appropriately be made. Note that in FIGS. 1 to 5, the left side corresponds to the distal end, which is to be inserted into the body, and the right side corresponds to the proximal end, which is to be operated by an operator such as a physician. Further, for easier understanding, smaller parts (such as a marker member 70 arranged inside a balloon 20) are shown in a somewhat exaggerated manner relative to the dimensions of other members. The same reference numbers are assigned in the figures for parts that are in common.

Figure 1:
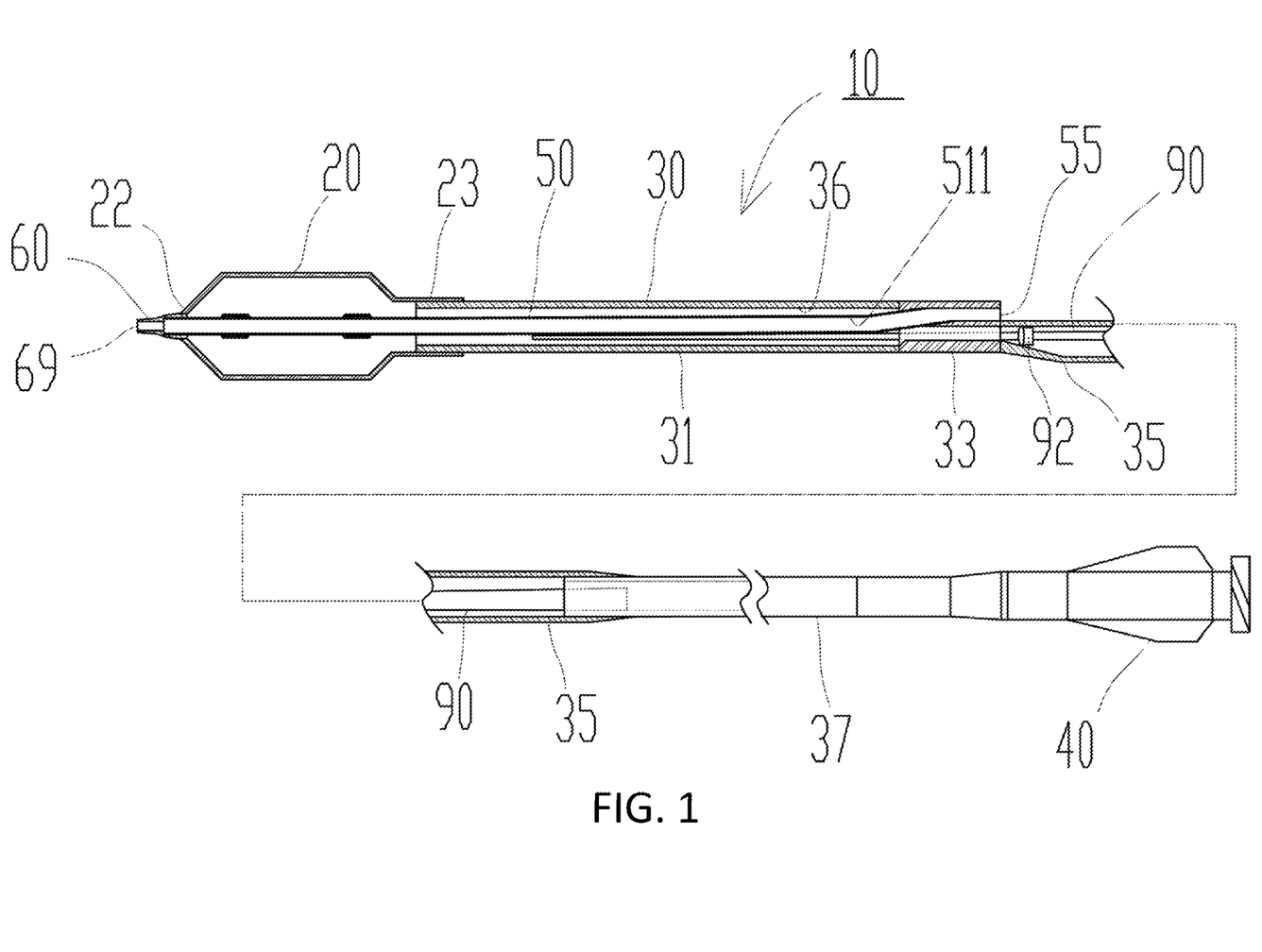
FIG. 1 shows a partial cross-sectional top view of a balloon catheter according to the disclosed embodiments.

A balloon catheter 10 of the disclosed embodiments can be used for treating a stenosis site inside a blood vessel of the heart and the like. The balloon catheter 10 comprises a balloon 20, an outer shaft 30, a connector 40, an inner shaft 50, and a tip 60, as shown in FIG. 1.

The balloon 20 serves to expand the stenosis site, and comprises a member made of a resin. In addition, a distal end of the balloon 20 includes a distal end attachment part 22, and a proximal end of the balloon 20 includes a proximal end attachment part 23. The distal end attachment part 22 is joined to a distal end of the inner shaft 50 through the tip 60, and the proximal end attachment part 23 is joined to a distal end of the outer shaft 30.

The outer shaft 30 serves to feed a fluid to the balloon 20, and comprises a tubular member which constitutes an inflation lumen 36 for feeding the fluid. Further, the outer shaft 30 has a distal end outer shaft portion 31, a guide wire port portion 33, a middle outer shaft portion 35, and a proximal end outer shaft portion 37 in that order from the distal end of the outer shaft 30. Note that the guide wire port portion 33 corresponds to a portion in which the distal end outer shaft portion 31, the middle outer shaft portion 35, and the inner shaft 50 are joined.

The inner shaft 50 is inserted into the distal end outer shaft portion 31, and the inflation lumen 36 is formed between the distal end outer shaft portion 31 and the inner shaft 50. Moreover, the proximal end outer shaft portion 37 comprises a metal tubular member referred to as a so-called hypotube. In addition, a distal end of the proximal end outer shaft portion 37 is inserted into and joined to a proximal end of the middle outer shaft portion 35. Further, the connector 40 is attached to a proximal end of the proximal end outer shaft portion 37. Accordingly, when a liquid for expanding the balloon 20 such as a contrast agent or physiological saline is fed from an indeflator (not shown) attached to the connector 40, the liquid flows into the balloon 20 through the inflation lumen 36, allowing the balloon 20 to expand.

Note that the distal end outer shaft portion 31 and the middle outer shaft portion 35 are preferably formed of a tube comprising a resin such as polyamide, polyamide elastomer, polyolefin, polyester, or polyester elastomer. Further, the proximal end outer shaft portion 37 is preferably configured with a superelastic alloy such as stainless steel (SUS304) or a Ni—Ti alloy.

Moreover, a core wire 90 is attached to an inner periphery of the distal end of the proximal end outer shaft portion 37. The core wire 90 has a circular cross-section, and is formed of a tapered metal wire with a diameter that decreases toward its distal end. In addition, the core wire 90 passes through the middle outer shaft portion 35 and the guide wire port portion 33, and extends into the distal end outer shaft portion 31. Further, the core wire 90 has a pressing member 92 positioned near and proximal to a proximal end of the guide wire port portion 33. Due to the positioning of the pressing member 92, when a pushing force and a rotating force are applied to the core wire 90, the pressing member 92 makes contact with the guide wire port portion 33, allowing the pushing force and the rotating force to be transmitted to the distal end outer shaft portion 31 and the inner shaft 50. Alternatively, the core wire 90 may directly make contact with the guide wire port portion 33 instead of contacting the guide wire port portion 33 with the pressing member 92. In this manner, when a pushing force and a rotating force are applied to the core wire 90, the pushing force and the rotating force can be transmitted to the distal end outer shaft portion 31 and the inner shaft 50. Note that the core wire 90 is preferably formed of a superelastic alloy such as stainless steel (SUS304) or an Ni—Ti alloy.

Further, a proximal end guide wire port 55 is formed at a proximal end of the inner shaft 50 by being joined to the guide wire port portion 33 of the outer shaft 30. Furthermore, a distal end guide wire port 69 is formed at the tip 60 arranged at the distal end of the inner shaft 50.

Figure 2:
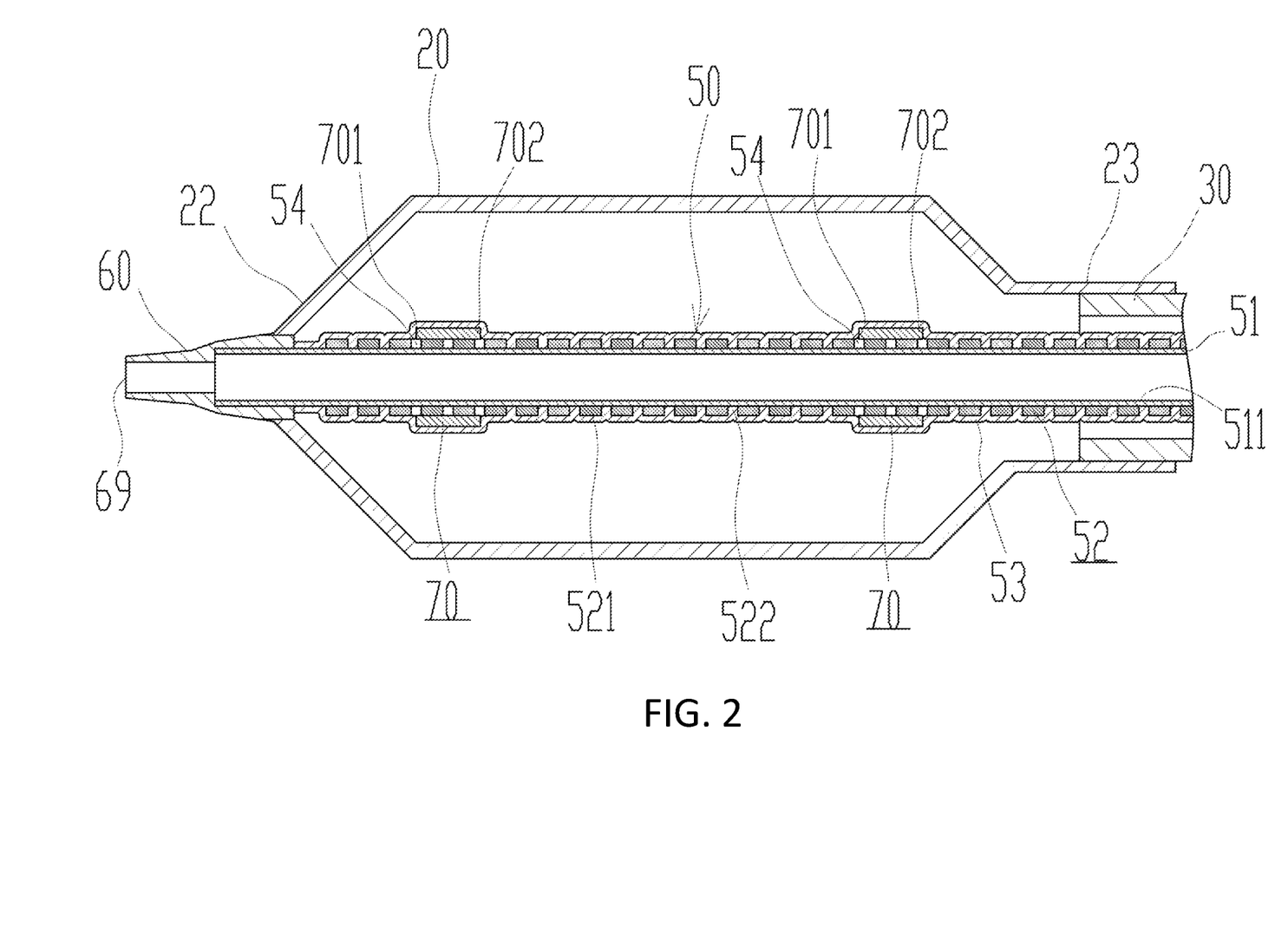
FIG. 2 shows a partial enlarged cross-sectional view of the balloon catheter of FIG. 1.

Moreover, as shown in FIG. 2, the inner shaft 50 has a tubular inner layer 51 in the inside thereof, the tubular inner layer 51 forming a guide wire lumen 511 for inserting a guide wire (not shown).

Moreover, a coil body 52 covering the inner layer 51 is arranged at an outer periphery of the inner layer 51. The coil body 52 has a sparsely wound portion 522 where a wire 521 with a rectangular cross-section is sparsely wound so that gaps are formed between adjacent windings of the wire 521.

Moreover, two marker members 70 with a cylindrical shape are arranged at each of a distal side and a proximal side of an outer periphery of the sparsely wound portion 522 of the coil body 52 in the inside of the balloon 20. Furthermore, an outer layer 53 covers the coil body 52 and the marker member 70.

Note that the inner layer 51 and the outer layer 53 are preferably formed of a resin such as polyethylene, polyurethane, polyamide, polyamide elastomer, polyolefin, polyester or polyester elastomer. Note that the coil body 52 is preferably formed of a superelastic alloy such as stainless steel (SUS304) or a Ni—Ti alloy. Moreover, the marker member 70 is preferably formed of a radiopaque metal material such as platinum or tungsten.

Further, the gaps between the adjacent windings of the wire 521 are filled with the outer layer 53 at a region between the adjacent windings of the wire 521 of the coil body 52 where the marker member 70 is not arranged. In contrast, in a region where the marker member 70 is arranged, a void 54 is formed between the adjacent windings of the wire 521 (that is, the adjacent windings of the wire 521 are not filled with the outer layer 53 in this region). In the balloon catheter 10, a distal end part 701 and a proximal end part 702 of the marker member 70 are each arranged at a position facing an unfilled gap, and thus the void 54 is formed at each of the distal end part 701 and the proximal end part 702 of the marker member.

Figure 3:
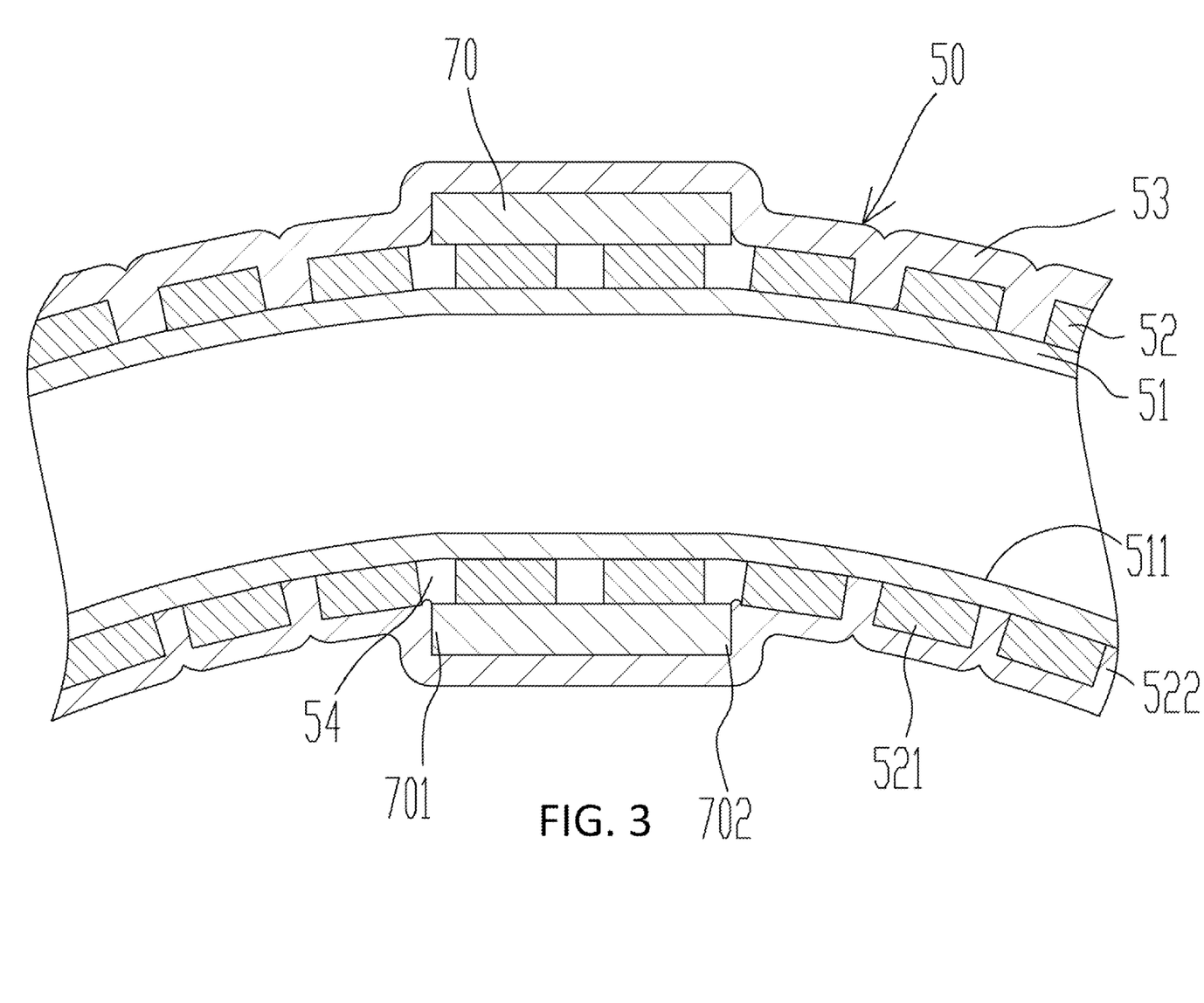
FIG. 3 shows a partial enlarged cross-sectional view illustrating a state of the balloon catheter of FIG. 1 when curved.

In the balloon catheter 10 having the above configuration, when the balloon catheter 10 is inserted into a curved blood vessel, the inner shaft 50 curves along with the blood vessel as shown in FIG. 3. At this time, at least a portion of the distal end part 701 and a portion of the proximal end part 702 of the marker member 70 can enter into the corresponding void 54 of the coil body 52 on the side of the curved inner shaft 50 that faces into the curve. Therefore, a stress concentration generated at a position where the marker member 70 is arranged can be relieved, preventing the inner shaft 50 from buckling. Further, the projection of the distal end part 701 and the proximal end part 702 of the marker member 70 toward the side of the inner periphery of the balloon 20 can also be controlled. Furthermore, the marker member 70 can be covered by the outer layer 53 without using another member. Therefore, the manufacturing process is simplified, and there is no risk of damaging the inner periphery of the balloon 20. Moreover, the outer layer 53 also serves to cover the marker member 70 and the coil body 52. Therefore, the outer diameter of the inner shaft 50 inside the balloon 20, as well as the diameter of the entire inner shaft 50, can be kept small.

In the balloon catheter 10, the void 54 is formed at each of the distal end part 701 and the proximal end part 702 of the marker member 70. However, buckling of the inner shaft 50 can be prevented even in the case of the configurations shown in FIGS. 4A and 4B. In these configurations, the void 54 is formed at only one of the distal end part 701 and the proximal end part 702 of the marker member 70.

Figure 4A:
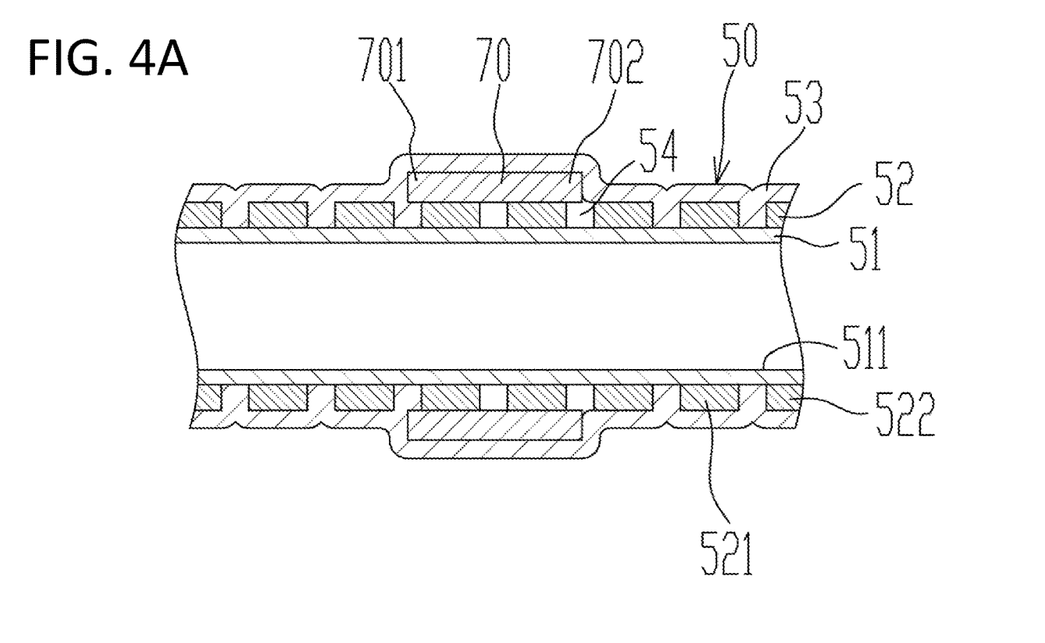
FIGS. 4A and 4B show partial enlarged cross-sectional views of a balloon catheter according to the disclosed embodiments.
Figure 4B:
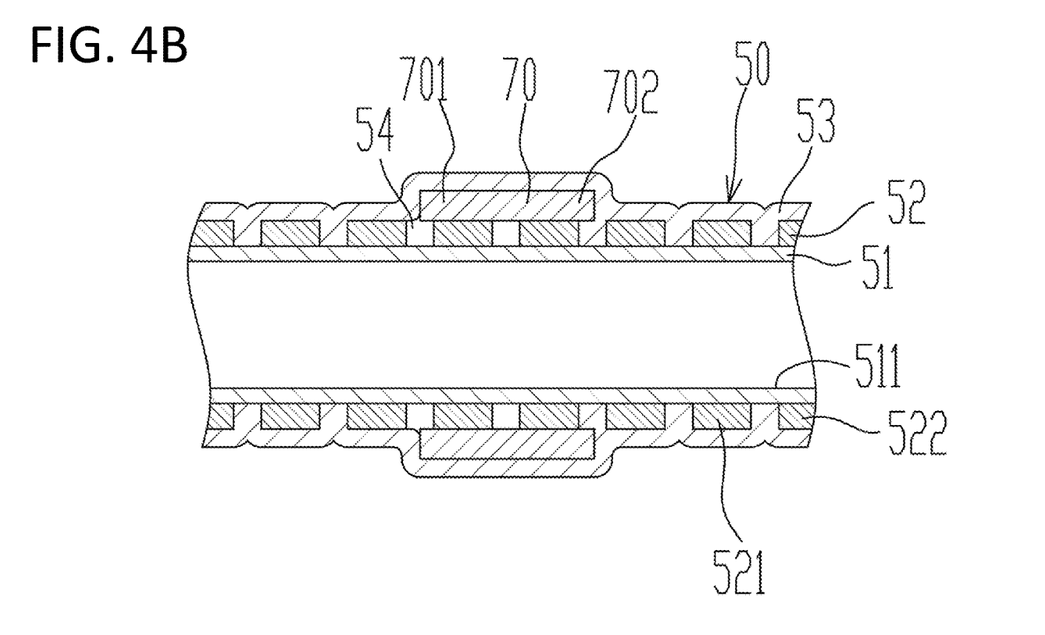

Specifically, only the proximal end part 702 of the marker member 70 is arranged at a position facing the void 54 in the configuration shown in FIG. 4A. In this case, the gaps between adjacent windings of the wire 521 facing the distal end part 701 of the marker member 70 are filled with the outer layer 53. In the configuration shown in FIG. 4B, only the distal end part 701 of the marker member 70 is arranged at a position facing the void part 54. In this case, the gaps between the adjacent windings of the wire 521 facing the proximal end part 702 of the marker member 70 are filled with the outer layer 53.

Figure 5:
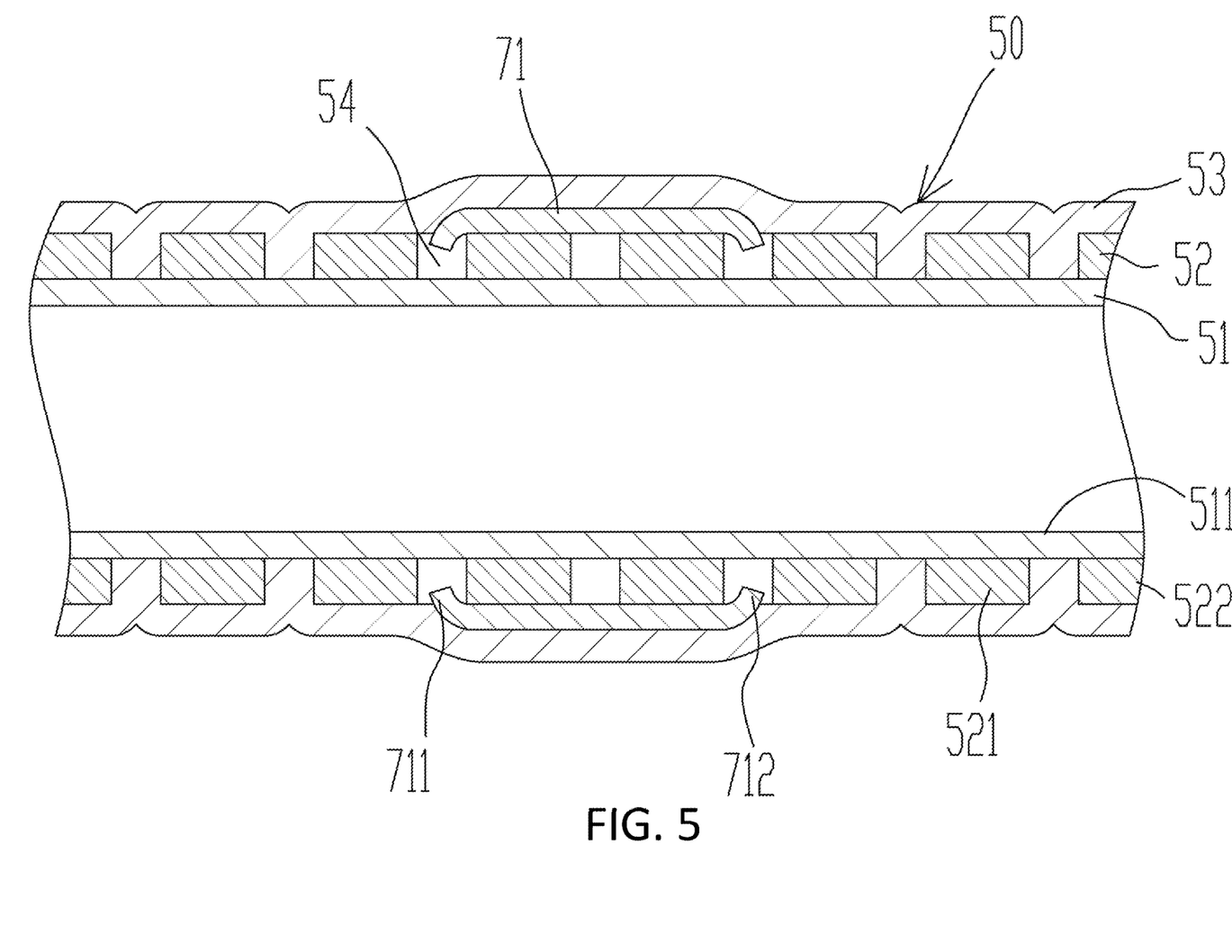
FIG. 5 shows a partial enlarged cross-sectional view of a balloon catheter according to the disclosed embodiments.

The balloon catheter 10 may include a marker member 71 in which a distal end part 711 and a proximal end part 712 each project toward the void 54 by curving inside (toward the void 54). In this configuration, the distal end part 711 and the proximal end part 712 form a smooth and continuous tapered shape. Therefore, a risk of damaging the inner periphery of the balloon 20 with the end portions (the distal end part 711 or the proximal end part 712) of the marker member 71 can be eliminated, preventing rupture (burst or breakage) of the balloon 20 due to contact with the marker member 71. Further, even in a case where the balloon catheter 10 curves and external force is therefore applied to the marker member 71, the end portions of the marker member 71 that have entered into the void 54 can make contact with the wire 521 of the coil body 52 to control the movement of the marker member 71. The end portions that have entered the void 54 may be curved such that the end portions reside completely inside the void.

In the configuration shown in FIG. 5, both the distal end part 711 and the proximal end part 712 of the marker member 71 are curved toward the inner layer 51. However, the marker member 71 may be formed so that only one of the distal end part 711 and the proximal end part 712 is curved toward the inner layer 51.

Figure 6A:
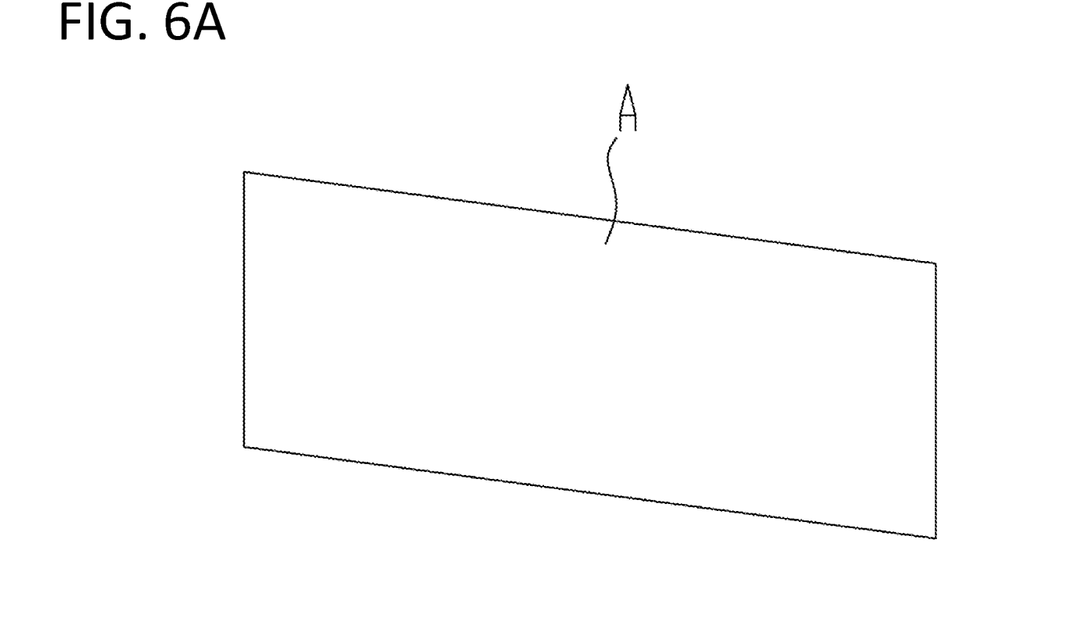
FIGS. 6A and 6B show diagrams illustrating a marker member of a balloon catheter according to of the disclosed embodiments.
Figure 6B:
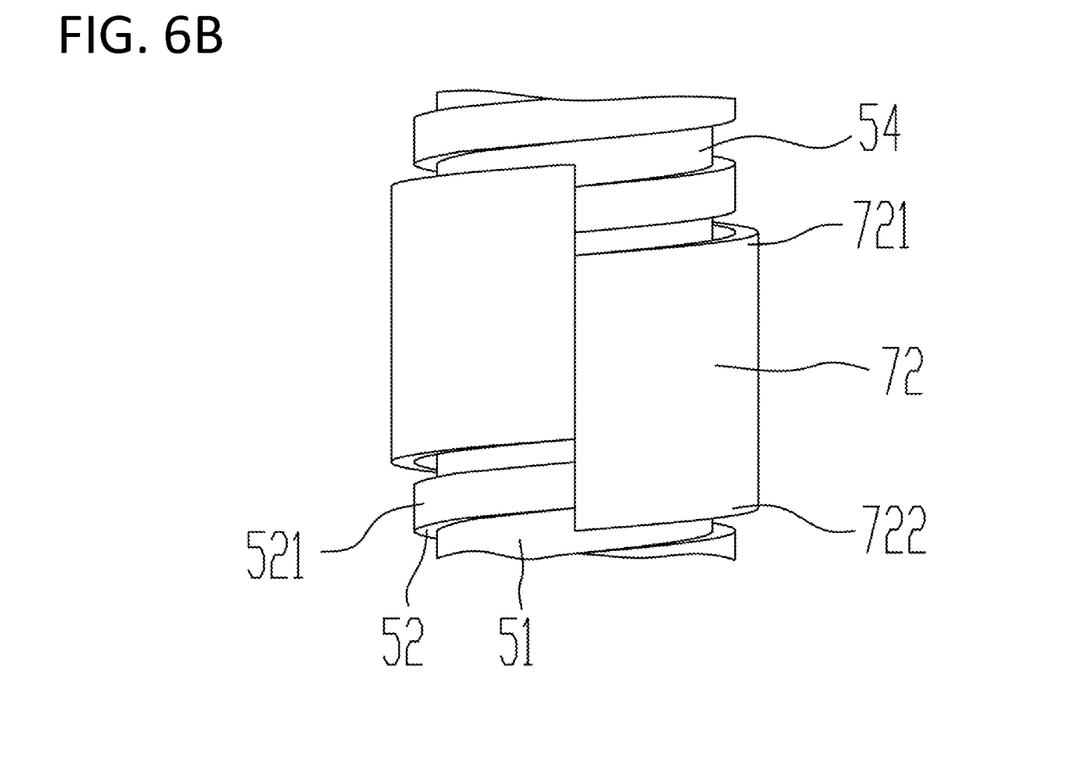

The balloon catheter 10 may include a marker member 72 formed by curving a parallelogram metal plate A, shown in plan view in FIG. 6A. In this case, as shown in FIG. 6B, a distal end part 721 and a proximal end part 722 of the marker member 72 are almost entirely arranged at a position facing the void 54. The distal end part 721 and the proximal end part 722 of the marker member 72 may be curved toward the inner layer 51.

In the balloon catheter 10, the number of the marker members 70 to 72 to be provided inside the balloon 20 may be one or more. Moreover, the cross-sectional shape of the wire 521 of the coil body 52 is not limited to a rectangular cross-section, but may be of other shapes such as a circular cross-section.

What is claimed is:

1. A balloon catheter comprising:
   a balloon; and
   an inner shaft joined to the balloon, the inner shaft comprising:
      an inner layer;
      a coil body arranged on an outer periphery of the inner layer and having a sparsely wound portion in which gaps are formed between adjacent windings of a wire forming the coil body;
      a marker member arranged on an outer periphery of the coil body at the sparsely wound portion without contacting the inner layer along an entire length of the marker member and having a distal end part and a proximal end part, and
      an outer layer covering the coil body and the marker member,
   wherein:
      at least one of the gaps forms a void such that the outer layer is not disposed in the void,
      at least one of the distal end part and the proximal end part of the marker member is arranged at a position facing the void without contacting the inner layer,
      at least one of a distal end surface and a proximal end surface of the marker member extends along a winding direction of the wire forming the coil body, and
      at least one of the distal end part and the proximal end part of the marker member is curved radially inward toward the inner layer and resides completely inside the void.

2. The balloon catheter according to claim 1, wherein the gaps between the adjacent windings of the coil body are filled with the outer layer in a region where the marker member is not arranged.

3. The balloon catheter according to claim 1, further comprising:
   an outer shaft,
   wherein:
      a distal end of the outer shaft is attached to a proximal end of the balloon,
      the inner shaft extends through the outer shaft and the balloon, and
      a distal end of the inner shaft is attached to a distal end of the balloon.

4. A balloon catheter comprising:
   a balloon; and
   an inner shaft joined to the balloon, the inner shaft comprising:
      an inner layer;

a coil body arranged on an outer periphery of the inner layer and having a sparsely wound portion in which gaps are formed between adjacent windings of a wire forming the coil body;

a marker member arranged on an outer periphery of the coil body at the sparsely wound portion without contacting the inner layer along an entire length of the marker member and having a distal end part and a proximal end part, and an outer layer covering the coil body and the marker member, wherein:

at least one of the gaps forms a void such that the outer layer is not disposed in the void, at least one of the distal end part and the proximal end part of the marker member is arranged at a position facing the void without contacting the inner layer, at least one of a distal end surface and a proximal end surface of the marker member extends along a winding direction of the wire forming the coil body, and both the distal end part and the proximal end part of the marker member are curved radially inward toward the inner layer and reside completely inside the void.

5. The balloon catheter according to claim 4, wherein the gaps between the adjacent windings of the coil body are filled with the outer layer in a region where the marker member is not arranged.

6. The balloon catheter according to claim 4, further comprising:

an outer shaft, wherein:

a distal end of the outer shaft is attached to a proximal end of the balloon, the inner shaft extends through the outer shaft and the balloon, and a distal end of the inner shaft is attached to a distal end of the balloon.

\* \* \* \* \*